United States Patent [19]
Abelson

[11] 4,315,024
[45] Feb. 9, 1982

[54] COMPOSITIONS AND METHOD FOR TREATING RED EYE

[75] Inventor: Mark B. Abelson, Andover, Mass.

[73] Assignee: Cooper Laboratories, Inc., Palo Alto, Calif.

[21] Appl. No.: 176,525

[22] Filed: Aug. 8, 1980

[51] Int. Cl.³ .................. A01N 43/50; A01N 43/56
[52] U.S. Cl. .................................................. 424/273 R
[58] Field of Search .................................... 424/273 R

[56] References Cited

U.S. PATENT DOCUMENTS

| 3,975,530 | 8/1976 | Durant et al. | 424/273 R |
| 4,013,659 | 3/1977 | Durant et al. | 424/273 R |
| 4,098,898 | 7/1978 | Durant et al. | 424/273 R |
| 4,104,382 | 8/1978 | Black et al. | 424/273 R |
| 4,112,234 | 9/1978 | Crenshaw et al. | 424/273 R |
| 4,200,760 | 4/1980 | Algieri et al. | 424/273 R |
| 4,220,653 | 9/1980 | Vivino | 424/273 R |

FOREIGN PATENT DOCUMENTS 54-106468 8/1979 Japan .............................. 424/273 R

OTHER PUBLICATIONS

Handbook of Ocular Pharmacology-2nd ed.-1978, Marvin Smith (Editor), pp. 25-27.

Primary Examiner—Douglas W. Robinson
Attorney, Agent, or Firm—Thomas R. Boland

[57] ABSTRACT

A method for treating red eye by administering to the afflicted eye a composition comprising an anti-inflammatory amount of an antagonist for $H_2$ receptors in the eye, preferably cimetidine, and a non-toxic, pharmaceutically acceptable, ophthalmological carrier.

3 Claims, No Drawings

COMPOSITIONS AND METHOD FOR TREATING RED EYE

BACKGROUND OF THE INVENTION

This invention relates to the treatment of inflammations of the surface tissues of the eye ("red eye") and more particularly to treatment of the ocular tissues by administering thereto anti-inflammatory effective amounts of antagonists for $H_2$ receptors.

Reddening or inflammation of the superficial tissues of the eye is a relatively common affliction since it usually accompanies various allergic reactions, such as hay fever allergies and the like, foreign body irritation in the eye, or eye fatigue. Such superficial conjunctival redness is generally the result of ciliary flush, dilation of the deep straight vessels of the episclera, and dilation of the superficial vessels of the conjunctiva.

Various types of palliative treatments have been used to treat this condition, but the most common treatment includes the administration of eye drops which contain emollients and other ingredients designed to ease the discomfort due to the inflammation and to eliminate the redness associated with the condition. Such prior treatments have not been entirely satisfactory, possibly due to the fact that the underlying causes of the dilation of the ocular blood vessels have not been completely understood, and no truly rational treatment of the condition has been previously proposed.

Recently, evidence has been discovered regarding the role of histamine in producing red eye. M. B. Abelson, et al., "Histamine and the Eye", in *Immunology and Immunopathology of the Eye*, A. M. Silverstein and G. R. O'Connor, Eds., Masson Publishing USA, Inc., 1979, pp. 362–364, have shown that histamine can produce the symptoms of redness and itching associated with ocular allergy. M. B. Abelson, et al., *Am. J. Ophthalmology*, 1977, Vol. 83, pp. 417–418, discloses that the tears of individuals afflicted with vernal conjunctivitis contain more histamine than the tears of normal individuals. However, there has been no suggestion in these publications that antagonists for $H_2$ receptors may be used in treating red eye.

Thus, a need has continued to exist for a simple, rational, and effective treatment for inflammation of superficial ocular tissue.

SUMMARY OF THE INVENTION

Accordingly, it is an object of the invention to provide a treatment for red eye, as well as to achieve an ocular anti-inflammatory effect therein through the use of antagonists for $H_2$ receptors.

These and other apparent objects of the invention are attained by administering to an individual afflicted with red eye an anti-inflammatory effective amount of an antagonist for histamine $H_2$ receptors in the superficial ocular tissue.

DETAILED DESCRIPTION OF THE INVENTION

By virtue of the discoveries that red eye is caused at least in part by the stimulation of the $H_2$ receptors in the superficial ocular tissue through the presence of histamine, and that the histamine receptors in the superficial ocular tissues are of the $H_2$ type, a basis has now been provided for a rational treatment of red eye. By administration of antagonists for histamine $H_2$ receptors, the action of $H_2$ agonists such as histamine is blocked, and the ocular condition caused by the presence of such agonists is relieved.

A preferred $H_2$ receptor antagonists is cimetidine, i.e., N-cyano-N'-methyl-N''-[2-[[(5-methyl-1H-imidazol-4-yl)methyl]-thio]ethyl]guanidine. This compound is already approved for use in humans in the treatment of peptic ulcer. Hence it is already known as a safe and effective antagonist for $H_2$ receptors in man.

The $H_2$ receptor antagonists used in practicing the method of treatment in this invention are preferably topically applied to the eye, e.g. by instillation of a solution of the $H_2$ antagonist in a suitable non-toxic ophthalmic vehicle. Aqueous ophthalmic solutions may be formulated, for example, in accord with the procedures set forth in chapter 83 of Remington's Pharmaceutical Sciences, 14th Edition, Mack Publishing Company. As such, they are sterile and may contain bacteriological preservatives to maintain sterility during use. The quaternary ammonium bacteriostats, for example, such as benzalkonium chloride, are suitable for this purpose.

Ointments may also be employed as vehicles for the $H_2$ antagonists used in the treatment of this invention. Such ointments may be prepared utilizing known pharmaceutical techniques with conventional petrolatum vehicles.

While topical administration of the $H_2$ antagonists to the afflicted tissues of the eye is the preferred method of administration, other routes for delivering the drug, such as oral or parenteral routes, are not excluded.

The effective amounts of $H_2$ antagonists used in accordance with this invention will vary depending on the potency of the selected antagonist. Where known $H_2$ antagonists are utilized, such as the preferred antagonist cimetidine, the effective amount is readily ascertained by one skilled in the art from simple experiments. By way of example, when utilizing cimetidine as the active ingredient the preferred concentration thereof in aqueous solution will be about 1% to about 2% by weight. Such a solution will be topically administered to humans in a dosage of 1–2 drops per eye.

Having generally described the invention, a more complete understanding can be obtained by reference to the following specific examples. These examples are presented for purposes of illustration only and they are not intended to be limiting unless otherwise specified.

EXAMPLE

Ten normal human subjects participated in the following study which demonstrated the presence of $H_2$ receptors in the ocular surface and showed that an $H_2$ antagonist, cimetidine, was effective in preventing red eye caused by administration of the $H_2$ agonist dimaprit.

During Phase I of the study, the right eye of each of the ten subjects was treated with one drop of the $H_2$ blocking agent cimetidine. After 3 minutes had elapsed both eyes were treated with one drop of dimaprit, an $H_2$ agonist. Subjects were evaluated using a slit lamp to observe injection and the presence or absence of chemosis. Photographs were taken to document the observed effects.

Phase II was undertaken a minimum of 48 hours after Phase I. During Phase II, the right eye of each of the same ten subjects was treated with one drop of the $H_1$ antagonist, antazoline. After 3 minutes had elapsed, both eyes were treated with one drop of dimaprit. Subjects were again evaluated at the slit lamp for injection and chemosis, and photographs were taken.

The photographs were evaluated in a double masked procedure by six judges. Injection was evaluated on a scale of 0 to 3 (0=no redness, 1=slight, 2=moderate, and 3=severe redness), using photographs taken before the treatment as controls.

The results of the evaluation for Phase I are shown in Table 1, and those for Phase II in Table 2.

TABLE 1

| SUBJECT | | Post cimetidine Judge No. | | | | | | Post dimaprit Judge No. | | | | | | Time of Observation post dimaprit |
|---|---|---|---|---|---|---|---|---|---|---|---|---|---|---|
| | | 1 | 2 | 3 | 4 | 5 | 6 | 1 | 2 | 3 | 4 | 5 | 6 | |
| 1 | OD | | | N.D. | | | | 0 | 0 | 0 | 0 | 0 | 0 | 10 min. |
| | OS | | | | | | | 2 | 2 | 2 | 1 | 1 | 1 | 10 min. |
| 2 | OD | | | N.D. | | | | 0 | 0 | 0 | 0 | 0 | 0 | 15 min. |
| | | | | | | | | 0 | 0 | 1 | 1 | 1 | 1 | 30 min. |
| | OS | | | | | | | 2 | 2 | 2 | 1 | 1 | 1 | 15 min. |
| | | | | | | | | 2 | 2 | 2 | 3 | 3 | 3 | 30 min. |
| 3 | OD | | | N.D. | | | | 0 | 0 | 0 | 0 | 0 | 0 | 18 min. |
| | | | | | | | | 0 | 1 | 1 | 1 | 1 | 1 | |
| | | | | | | | | 0 | 0 | 0 | 0 | 0 | 0 | 30 min. |
| | OS | | | | | | | 1 | 2 | 2 | 2 | 2 | 2 | 18 min. |
| | | | | | | | | 2 | 2 | 2 | 2 | 2 | 2 | |
| | | | | | | | | 1 | 1 | 1 | 1 | 1 | 1 | 30 min. |
| 4 | OD | | | N.D. | | | | 0 | 0 | 0 | 0 | 0 | 0 | 15 min. |
| | | | | | | | | 0 | 0 | 0 | 0 | 0 | 0 | |
| | | | | | | | | 0 | 0 | 0 | 0 | 0 | 0 | 30 min. |
| | OS | | | | | | | 1 | 1 | 1 | 1 | 1 | 1 | 15 min. |
| | | | | | | | | 2 | 2 | 2 | 2 | 2 | 2 | |
| | | | | | | | | 2 | 2 | 2 | 2 | 1 | 1 | 30 min. |
| 5 | OD | | | N.D. | | | | 1 | 1 | 1 | 1 | 1 | 1 | |
| | | | | | | | | 1 | 1 | 1 | 1 | 1 | 2 | 10 min. |
| | | | | | | | | 2 | 2 | 2 | 2 | 2 | 2 | |
| | | | | | | | | 2 | 2 | 2 | 2 | 2 | 1 | 30 min. |
| | OS | | | | | | | 3 | 3 | 3 | 3 | 3 | 3 | |
| | | | | | | | | 2 | 2 | 2 | 2 | 2 | 3 | 10 min. |
| | | | | | | | | 3 | 3 | 3 | 3 | 3 | 3 | |
| | | | | | | | | 3 | 3 | 3 | 3 | 3 | 3 | 30 min. |
| 6 | OD | | | N.D. | | | | 2 | 2 | 2 | 2 | 2 | 2 | |
| | | | | | | | | 1 | 1 | 1 | 1 | 1 | 1 | 10 min. |
| | | | | | | | | 2 | 2 | 2 | 2 | 3 | 3 | |
| | | | | | | | | 2 | 2 | 2 | 2 | 2 | 2 | 30 min. |
| | OS | | | | | | | 3 | 3 | 3 | 3 | 3 | 3 | |
| | | | | | | | | 2 | 2 | 2 | 2 | 2 | 2 | 10 min. |
| | | | | | | | | 3 | 3 | 3 | 3 | 3 | 3 | |
| | | | | | | | | 3 | 3 | 3 | 3 | 3 | 3 | 30 min. |
| 7 | OD | | | N.D. | | | | 1 | 1 | 1 | 1 | 1 | 1 | |
| | | | | | | | | 1 | 1 | 1 | 1 | 1 | 1 | 20 min. |
| | OS | | | | | | | 2 | 2 | 2 | 2 | 2 | 2 | |
| | | | | | | | | 1 | 1 | 1 | 1 | 1 | 1 | 20 min. |
| 8 | OD | 0 | 0 | 0 | 0 | 0 | 0 | 1 | 1 | 1 | 1 | 1 | 1 | |
| | | | | | | | | 1 | 1 | 1 | 1 | 0 | 0 | 20 min. |
| | OS | | | | | | | 1 | 1 | 1 | 1 | 1 | 1 | |
| | | | | | | | | 1 | 1 | 1 | 1 | 1 | 1 | 20 min. |
| 9 | OD | 0 | 0 | 0 | 0 | 0 | 0 | 0 | 1 | 1 | 1 | 1 | 1 | |
| | | | | | | | | 0 | 0 | 0 | 0 | 0 | 1 | 15 min. |
| | | | | | | | | 0 | 0 | 0 | 0 | 0 | 0 | 30 min. |
| | OS | | | | | | | 1 | 1 | 1 | 1 | 2 | 2 | |
| | | | | | | | | 1 | 1 | 1 | 1 | 1 | 1 | 15 min. |
| | | | | | | | | 1 | 1 | 1 | 1 | 1 | 1 | 30 min. |
| 10 | OD | 0 | 0 | 0 | 0 | 0 | 0 | 1 | 1 | 1 | 1 | 1 | 1 | |
| | | | | | | | | 0 | 0 | 0 | 1 | 1 | 1 | 10 min. |
| | | | | | | | | 1 | 1 | 1 | 1 | 1 | 1 | |
| | | | | | | | | 1 | 1 | 1 | 1 | 1 | 1 | 25 min. |
| | OS | | | | | | | 2 | 2 | 2 | 2 | 2 | 2 | |
| | | | | | | | | 1 | 1 | 1 | 1 | 2 | 2 | 10 min. |
| | | | | | | | | 2 | 2 | 3 | 3 | 3 | 3 | |
| | | | | | | | | 2 | 2 | 2 | 2 | 2 | 2 | 25 min. |

TABLE 2

| SUBJECT | | Post antazoline Judge No. | | | | | | Post dimaprit Judge No. | | | | | | Time of Observation post dimaprit |
|---|---|---|---|---|---|---|---|---|---|---|---|---|---|---|
| | | 1 | 2 | 3 | 4 | 5 | 6 | 1 | 2 | 3 | 4 | 5 | 6 | |
| 1 | OD | 0 | 0 | 0 | 0 | 0 | 0 | 2 | 2 | 2.5 | 3 | 3 | | |
| | | | | | | | | 2 | 2 | 2 | 2 | 2 | 1 | 30 min. |
| | OS | | | | | | | 3 | 3 | 3 | 3 | 2.5 | | |
| | | | | | | | | 2 | 2 | 1.5 | 1 | 1 | 1 | 30 min. |
| 2 | OD | | | N.D. | | | | 1 | 1.5 | 1.5 | 1.5 | 2 | | |
| | | | | | | | | 1 | 1 | 1 | 1 | 1 | | 10 min. |
| | OS | | | | | | | 2 | 2 | 2 | 2 | 2 | 2 | |

TABLE 2-continued

| | | | Post antazoline Judge No. | | | | | | EVALUATION Post dimaprit Judge No. | | | | | Time of Observation post dimaprit |
|---|---|---|---|---|---|---|---|---|---|---|---|---|---|---|
| SUBJECT | 1 | 2 | 3 | 4 | 5 | 6 | 1 | 2 | 3 | 4 | 5 | 6 | |
| | | | | | | | 2 | 2 | 2 | 2 | 1.5 | | 10 min. |
| 3 OD | 0 | 0 | 0 | 0 | 0 | 1 | 2 | 2 | 2 | 2 | 2 | 2 | |
| | | | | | | | 0 | 1 | 1 | 1 | 1 | 1 | 20 min. |
| | | | | | | | 1 | 1 | 1 | 1 | 1 | 1 | 25 min. |
| OS | | | | | | | 2 | 2 | 2 | 2 | 2 | 2 | |
| | | | | | | | 1 | 1 | 1 | 1 | 1 | 1 | 20 min. |
| | | | | | | | 1 | 1 | 1 | 1 | 1 | 1 | 25 min. |
| 4 OD | 0 | 0 | 0 | 0 | 0 | 0 | 1 | 1 | 1 | 1 | 1 | 1 | 15 min. |
| OS | | | | | | | 1 | 1 | 1 | 1 | 1 | 1 | 15 min. |
| 5 OD | 0 | 0 | 0 | 0 | 0 | 1 | 2 | 2 | 2 | 2 | 2 | 2 | 10 min. |
| | | | | | | | 3 | 3 | 3 | 3 | 3 | 3 | 15 min. |
| OS | | | | | | | 2 | 2 | 2 | 2 | 2 | 2 | 10 min. |
| | | | | | | | 2 | 2 | 3 | 3 | 3 | 3 | 15 min. |
| 6 OD | 0 | 0 | 0 | 0 | 0 | 1 | 3 | 3 | 3 | 3 | 3 | 3 | |
| | | | | | | | 2 | 2 | 2 | 2 | 2 | 2 | 10 min. |
| | | | | | | | 3 | 3 | 3 | 3 | 3 | 3 | |
| | | | | | | | 2 | 3 | 3 | 3 | 3 | 3 | 25 min. |
| OS | | | | | | | 2 | 2 | 2 | 2 | 2 | 2 | |
| | | | | | | | 1 | 1 | 1 | 1 | 1 | 2 | 10 min. |
| | | | | | | | 3 | 3 | 3 | 3 | 3 | 3 | |
| | | | | | | | 2 | 3 | 3 | 3 | 3 | 3 | 25 min. |
| 7 OD | 0 | 0 | 0 | 0 | 0 | 0 | 2 | 2 | 2 | 2 | 2 | 2 | |
| | | | | | | | 2 | 2 | 2 | 2 | 2 | 2 | 10 min. |
| | | | | | | | 2 | 2 | 2 | 2 | 2 | 2 | |
| | | | | | | | 2 | 2 | 2 | 2 | 2 | 2 | 25 min. |
| OS | | | | | | | 1 | 1 | 1 | 1 | 1 | 1 | |
| | | | | | | | 1 | 1 | 1 | 1 | 1 | 1 | 10 min. |
| | | | | | | | 1 | 1 | 1 | 1 | 1 | 1 | |
| | | | | | | | 1 | 1 | 1 | 1 | 1 | 1 | 25 min. |
| 8 OD | 0 | 0 | 0 | 0 | 0 | 1 | 3 | 3 | 3 | 3 | 3 | 3 | |
| | | | | | | | 2 | 2 | 2 | 2 | 2 | 2 | 10 min. |
| | | | | | | | 2 | 2 | 2 | 2 | 2 | 3 | |
| | | | | | | | 1 | 1 | 1 | 1 | 2 | 2 | 25 min. |
| OS | | | | | | | 2 | 2 | 2 | 2 | 2 | 2 | |
| | | | | | | | 1 | 1 | 1 | 1 | 1 | 1 | 10 min. |
| | | | | | | | 2 | 2 | 2 | 2 | 2 | 2 | |
| | | | | | | | 1 | 1 | 1 | 1 | 2 | 2 | 25 min. |
| 9 OD | 0 | 0 | 0 | 0 | 0 | 0 | 2 | 2 | 2 | 2 | 2 | 2 | |
| | | | | | | | 2 | 2 | 2 | 1 | 1 | 1 | 15 min. |
| | | | | | | | 2 | 2 | 2 | 2 | 3 | 3 | |
| | | | | | | | 1 | 1 | 1 | 1 | 1 | 1 | 30 min. |
| OS | | | | | | | 1 | 2 | 2 | 2 | 2 | 2 | |
| | | | | | | | 1 | 1 | 1 | 1 | 1 | 1 | 15 min. |
| | | | | | | | 2 | 2 | 2 | 2 | 3 | 3 | |
| | | | | | | | 1 | 1 | 1 | 1 | 1 | 1 | 30 min. |
| 10 OD | 1 | 1 | 1 | 1 | 1 | 1 | 3 | 3 | 3 | 3 | 3 | 3 | |
| | | | | | | | 2 | 2 | 2 | 2 | 2 | 2 | 10 min. |
| | | | | | | | 2 | 3 | 3 | 3 | 3 | 3 | |
| | | | | | | | 2 | 2 | 2 | 2 | 2 | 2 | 25 min. |
| OS | | | | | | | 2 | 2 | 2 | 2 | 2 | 2 | |
| | | | | | | | 1 | 1 | 1 | 1 | 1 | 1 | 10 min. |
| | | | | | | | 2 | 2 | 3 | 3 | 3 | 3 | |
| | | | | | | | 1 | 1 | 1 | 2 | 2 | 2 | 25 min. |

The results of the study were evaluated by computing the mean and standard deviation for each subject in each eye and performing a paired t-test to compare the mean values in OD and OS in Phase I and Phase II respectively. The results were as follows:

| | PHASE I | PHASE II |
|---|---|---|
| Mean Difference | 1.033 | −0.152 |
| Standard Deviation | 0.072 | 0.071 |
| t Statistic | 14.28 | 2.135 |
| P-Value | <.001 | $0.02 < P < 0.05$ |

The results are statistically significant in both instances. However, the difference is very small in Phase II. The results demonstrate that $H_2$ receptors are present in the ocular surface tissues, and that administration of cimetidine is an effective method of preventing red eye produced by agonists for $H_2$ receptors.

This, of course, indicates that cimetidine is an effective agent in the treatment of red eye and the $H_2$ antagonists would generally be effective in the treatment of red eye.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A method of treating red eye comprising topically administering to the eye a therapeutic amount of an $H_2$ antagonist which is effective to substantially reduce the red appearance of the eye.

2. The method of claim 1 wherein said $H_2$ antagonist is cimetidine.

3. The method of claim 1 wherein said $H_2$ antagonist is administered topically in a composition comprising said antagonist and a non-toxic, pharmaceutically acceptable, ophthalmological carrier.

* * * * *